United States Patent
Sugimoto et al.

(10) Patent No.: US 11,230,513 B2
(45) Date of Patent: Jan. 25, 2022

(54) PRODUCTION PROCESS OF 1,3-BUTADIENE (71) Applicants: JSR Corporation, Tokyo (JP); ENEOS CORPORATION, Tokyo (JP)

(72) Inventors: Mayu Sugimoto, Minato-ku (JP); Yuichiro Sasaki, Minato-ku (JP); Sosuke Higuchi, Chiyoda-ku (JP); Nobuhiro Kimura, Chiyoda-ku (JP)

(73) Assignees: JSR Corporation, Tokyo (JP); ENEOS CORPORATION, Tokyo (JP)

( * ) Notice: Subject to any disclaimer, the term of this patent is extended or adjusted under 35 U.S.C. 154(b) by 0 days.

(21) Appl. No.: 17/013,028

(22) Filed: Sep. 4, 2020

(65) Prior Publication Data
US 2020/0399191 A1 Dec. 24, 2020

Related U.S. Application Data (63) Continuation of application No. PCT/JP2019/008623, filed on Mar. 5, 2019.

(51) Int. Cl.
*C07C 5/48* (2006.01)
*C07C 7/11* (2006.01)

(52) U.S. Cl.
CPC . *C07C 5/48* (2013.01); *C07C 7/11* (2013.01)

(58) Field of Classification Search
CPC ........... C07C 11/167; C07C 5/48; C07C 7/11; C07C 7/005; C07C 7/08; B01J 21/08; B01J 21/10; B01J 23/30
See application file for complete search history.

(56) References Cited

U.S. PATENT DOCUMENTS 9,957,208 B2 * 5/2018 Grune ..................... C07C 5/48

FOREIGN PATENT DOCUMENTS

| JP | 2012-111751 A | 6/2012 |
| JP | 5621304 B2 | 11/2014 |
| JP | 5652151 B2 | 1/2015 |

(Continued)

OTHER PUBLICATIONS

International Search Report dated May 21, 2019 in PCT/JP2019/008623 filed Mar. 5, 2019, 1 page.

(Continued)

*Primary Examiner* — Sharon Pregler
(74) *Attorney, Agent, or Firm* — Oblon, McClelland, Maier & Neustadt, L.L.P.

(57) ABSTRACT

A process of producing 1,3-butadiene includes: a first step of obtaining gases containing 1,3-butadiene by an oxidative dehydrogenation reaction of a raw material gas with a molecular oxygen-containing gas in the presence of a metal oxide catalyst, the raw material gas containing 1-butene and 2-butene and having a proportion of 2-butene to a sum of 1-butene and 2-butene, which is defined as 100% by volume, being not less than 50% by volume; a second step of cooling the produced gases obtained in the first step; and a third step of separating the produced gases having undergone the second step into molecular oxygen and inert gases and other gases containing 1,3-butadiene by selective absorption to an absorbing solvent, wherein the concentration of methyl vinyl ketone in the produced gases having been cooled in the second step is 0% by volume or more and not more than 0.03% by volume.

20 Claims, 1 Drawing Sheet (56) References Cited

FOREIGN PATENT DOCUMENTS

| | | |
|---|---|---|
| JP | 5714857 B2 | 5/2015 |
| JP | 2016-500333 A | 1/2016 |
| JP | 2016-503073 A | 2/2016 |
| JP | 2017-533931 A | 11/2017 |
| WO | WO 2015/087668 A1 | 6/2015 |

OTHER PUBLICATIONS

Indian Office Action dated Dec. 4, 2020 in Indian Patent Application No. 202037042370 (with English translation), 6 pages.

\* cited by examiner

PRODUCTION PROCESS OF 1,3-BUTADIENE

TECHNICAL FIELD

The present invention relates to a process of producing 1,3-butadiene, and more particularly, to a process of producing 1,3-butadiene utilizing an oxidative dehydrogenation reaction.

BACKGROUND ART

Conventionally, there has been adopted, as a process of producing 1,3-butadiene (hereinafter simply referred to as "butadiene"), a process of separating components other than butadiene from a fraction having 4 carbon atoms obtained by cracking of naphtha (hereinafter also referred to as "C4 fraction") by distillation.

Although demand for butadiene is increasing as a raw material for synthetic rubber and the like, the supply amount of the C4 fraction has been reduced due to a situation such as a shift in a process of producing ethylene from a process by cracking of naphtha to a process by thermal decomposition of ethane. Thus, production of butadiene not using the C4 fraction as a raw material is investigated.

Therefore, as a process of producing butadiene, a process of separating butadiene from a product gas obtained by oxidative dehydrogenation of n-butene has attracted attention. As the production process, in order to improve the separation efficiency of butadiene, a method has been studied in which a pressure of a product gas of an oxidative dehydrogenation reaction is increased and then butadiene is separated using an absorbing solvent (see Patent Literature 1 to Patent Literature 5).

CITATION LIST

Patent Literature

Patent Literature 1: Japanese Patent No. 5621304
Patent Literature 2: Japanese Patent No. 5652151
Patent Literature 3: Japanese Patent No. 5714857
Patent Literature 4: Japanese Patent Application Laid-Open No. 2012-111751
Patent Literature 5: Japanese Translation of PCT Patent Application Publication No. 2016-500333

SUMMARY OF INVENTION

Technical Problem

However, the above-mentioned conventional process of producing butadiene has a problem in that adhering substances generated in a production process adhere to tools used, resulting in a decrease in purification efficiency. More specifically, in the step of desolventizing, adhering substances are generated in the desolventizing tower (reboiler) used, and so the purification efficiency is lowered.

Thus, as a result of repeated studies by the inventors of the present invention on a process of producing 1,3-butadiene utilizing an oxidative dehydrogenation reaction, it has been revealed that most of the adhering substances in a tool used in a production process is derived from a specific compound among by-products of an oxidative dehydrogenation reaction.

The present invention has been made in view of the foregoing circumstances and has as its object the provision of a process of producing 1,3-butadiene which is capable of reducing the generation of adhering substances in a tool used in a production process.

Solution to Problem

The process of producing 1,3-butadiene according to the present invention includes: a first step of obtaining gases containing 1,3-butadiene by an oxidative dehydrogenation reaction of a raw material gas with a molecular oxygen-containing gas in the presence of a metal oxide catalyst, the raw material gas containing 1-butene and 2-butene and having a proportion of 2-butene to a sum of 1-butene and 2-butene, which is defined as 100% by volume, being not less than 50% by volume;

a second step of cooling the produced gases obtained in the first step; and a third step of separating the produced gases having undergone the second step into molecular oxygen and inert gases and other gases containing 1,3-butadiene by selective absorption to an absorbing solvent, wherein the concentration of methyl vinyl ketone in the produced gases having been cooled in the second step is 0% by volume or more and not more than 0.03% by volume.

In the process of producing 1,3-butadiene according to the present invention, in the produced gases having been cooled in the second step, the concentration of molecular nitrogen may preferably be not less than 60% by volume and not more than 94% by volume, the concentration of the sum of 1-butene and 2-butene may preferably be 0% by volume or more and not more than 2% by volume, the concentration of 1,3-butadiene may preferably be not less than 2% by volume and not more than 15% by volume, and the concentration of ketones and aldehydes may preferably be 0% by volume or more and not more than 0.3% by volume.

In the process of producing 1,3-butadiene according to the present invention, in the second step, the produced gases may preferably be cooled by being brought into contact with a cooling medium, and a concentration of an organic acid in the cooling medium having been in contact with the produced gases may preferably be not more than 7% by mass.

In the process of producing 1,3-butadiene according to the present invention, the pressure in the first step may preferably be not less than 0.1 MPaG and not more than 0.4 MPaG, the pressure in the second step may preferably be not more than the pressure in the first step, and the pressure in the third step may preferably be not more than the pressure in the second step.

In the process of producing 1,3-butadiene according to the present invention, the molecular oxygen and inert gases obtained in the third step may preferably be flown back to the first step, and the concentration of the molecular nitrogen in the gases to be flown back from the third step to the first step may preferably be not less than 87% by volume and not more than 97% by volume, and the concentration of the molecular oxygen therein may preferably be not less than 1% by volume and not more than 6% by volume.

Advantageous Effects of Invention

According to the process of producing 1,3-butadiene of the present invention, the use of gases having a specific composition as a raw material gas can lead to suppress the production of methyl vinyl ketone which is a by-product of an oxidative dehydrogenation reaction. As a result, the generation of adhering substances in the tool used in the production process is reduced.

In the process of producing 1,3-butadiene according to the present invention, the pressure in the first step is adjusted to fall within a specific range, and the pressure in the second step and the pressure in the third step are each adjusted to be not more than the pressure in the preceding step, and so the reaction efficiency of the oxidative dehydrogenation reaction can be improved and the energy consumption can be reduced.

DESCRIPTION OF EMBODIMENTS

Figure 1:
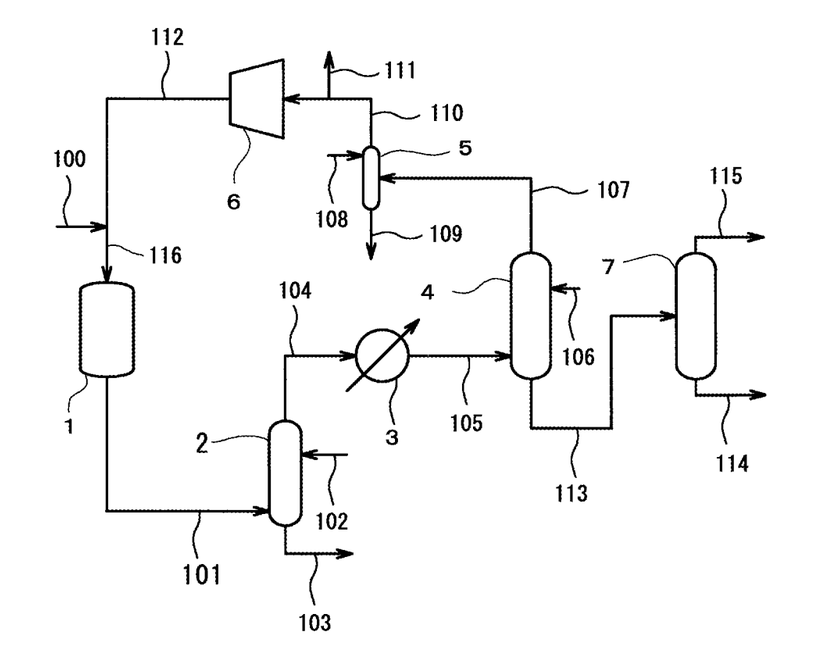
The FIGURE is a flow diagram illustrating an example of a specific method of carrying out the production process of butadiene according to the present invention.

Hereinafter, embodiments of the present invention will be described.

The process of producing butadiene (1,3-butadiene) according to the present invention has the steps shown in (1) to (3) below, and is to produce butadiene from a raw material gas containing 1-butene and 2-butene by subjecting the gas to the steps (1) to (3) described below.

Herein, "2-butene" encompasses cis-2-butene and trans-2-butene.

(1) A first step of obtaining produced gases containing 1,3-butadiene by an oxidative dehydrogenation reaction of a raw material gas containing 1-butene and 2-butene with a molecular oxygen-containing gas, (2) A second step of cooling the produced gases obtained in the first step, and (3) A third step of separating the produced gases having undergone the second step into molecular oxygen and inert gases and other gases containing 1,3-butadiene by selective absorption to an absorbing solvent.

Then, in the process of producing butadiene according to the present invention, the raw material gas contains 1-butene and 2-butene. The proportion of 2-butene to the sum of 1-butene and 2-butene, which is defined as 100% by volume, in the raw material gas is not more than 50% by volume, preferably not more than 70% by volume, more preferably not more than 85% by volume.

If the proportion of 2-butene is too small, the concentration of methyl vinyl ketone in the produced gases increases. Thus, adhering substances derived from methyl vinyl ketone may tend to be generated in tools used in the next and subsequent steps. Specifically, in particular, when an absorbing solvent is circulated and used, an adhering substance derived from methyl vinyl ketone is likely to be generated in tools used in a desolventizing step described later.

In the process of producing butadiene according to the present invention, the produced gases having undergone the second step, that is, the produced gases having been cooled in the second step, has a concentration of methyl vinyl ketone of 0% by volume or more and not more than 0.03% by volume, preferably 0% by volume or more and not more than 0.02% by volume.

As a preferred specific example of the process of producing butadiene according to the present invention, as illustrated in the FIGURE, may be mentioned a method of separating the produced gases having undergone the second step by causing an absorbing solvent to selectively absorb other gases containing 1,3-butadiene in the third step.

Hereinafter, a specific example of a process of producing butadiene according to the present invention will be described in detail using the FIGURE.

The FIGURE is a flow diagram illustrating an example of a specific method of carrying out the process of producing butadiene according to the present invention.

The process of producing butadiene according to the present invention illustrated in the FIGURE includes the steps of (1) to (3) described above as well as a desolventizing step of subjecting the absorbing solvent that was obtained in the third step and has absorbed other gases containing 1,3-butadiene to a solvent separation treatment, and a circulation step of flowing back molecular oxygen and inert gases obtained in the third step to the first step, that is, feeding them as a recirculation gas.

In the process of producing butadiene according to the present invention illustrated in the FIGURE, the absorbing solvent fed to the third step is circulated and used.

First Step:

In the first step, the raw material gas and the molecular oxygen-containing gas are subjected to an oxidative dehydrogenation reaction in the presence of a metal oxide catalyst to obtain produced gases containing butadiene (1,3-butadiene). In this first step, the oxidative dehydrogenation reaction of the raw material gas and the molecular oxygen-containing gas is performed by a reactor vessel 1, as illustrated in the FIGURE. Herein, the reactor vessel 1 is a tower having a gas inlet provided at an upper portion thereof and a gas outlet provided at a lower portion thereof, and a catalyst layer (not illustrated) formed by being filled with a metal oxide catalyst thereinside. In the reactor vessel 1, the gas inlet is connected to a piping 100 and a piping 112 via a piping 116. The gas outlet is connected to a piping 101.

More specifically, in the first step, the raw material gas, the molecular oxygen-containing gas, and, as necessary, inert gases and water (water vapor) (hereinafter collectively referred to as "new supply gas") are supplied to the reactor vessel 1 via the piping 100 communicating with the piping 116. The new supply gas, before being introduced into the reactor vessel 1, is heated to about not lower than 200° C. and about not higher than 400° C. by a preheater (not illustrated) disposed between the reactor vessel 1 and the piping 100. The reactor vessel 1 is supplied with the recirculation gas from the circulation step after being heated by the preheater via the piping 112 communicating with the piping 116 together with the new supply gas supplied via the piping 100. That is, a mixed gas of the new supply gas and the recirculation gas is supplied to the reactor vessel 1 after being heated by the preheater. Here, the new supply gas and the recirculation gas may be directly supplied to the reactor vessel 1 from separate pipings, but may preferably be supplied in a mixed state from the common piping 116, as illustrated in the FIGURE. The provision of the common piping 116 can lead to supply a mixed gas containing various components in a state of being mixed uniformly in advance to the reactor vessel 1, and so a situation in which a non-uniform mixed gas partially forms a detonating gas in the reactor vessel 1 can be prevented, and the like.

Then, in the reactor vessel 1 to which the mixed gas has been supplied, butadiene (1,3-butadiene) is generated by an oxidative dehydrogenation reaction of the raw material gas and the molecular oxygen-containing gas to obtain produced gases containing the target butadiene. The resulting produced gases flow out of the gas outlet of the reactor vessel 1 into the piping 101.

Raw Material Gas:

The raw material gas is a gaseous material obtained by gasifying n-butene (1-butene and 2-butene), which is a raw material for 1,3-butadiene and is a monoolefin having 4 carbon atoms, by a vaporizer (not illustrated), and contains 1-butene and 2-butene as described above, and has the proportion of 2-butene to the sum of 1-butene and 2-butene, which is defined as 100% by volume, being not less than 50% by volume. This raw material gas is a flammable gas having flammability.

In the raw material gas, the concentration of the sum of 1-butene and 2-butene is usually not less than 40% by volume, preferably not less than 60% by volume, more preferably not less than 75% by volume, and particularly preferably not less than 95% by volume.

The raw material gas may contain optional impurities within a range that does not inhibit the effect of the present invention. As specific examples of the impurities, may be mentioned a branched monoolefin such as i-butene, and a saturated hydrocarbon such as propane, n-butane and i-butane. The raw material gas may contain, as an impurity, 1,3-butadiene which is a target product. The amount of impurities in the raw material gas is usually not more than 60% by volume, preferably not more than 40% by volume, more preferably not more than 25% by volume, and particularly preferably not more than 5% by volume per 100% by volume of the raw material gas. If the amount of impurities contained is too large, the reaction rate tends to be reduced due to a decrease in the concentration of the sum of 1-butene and 2-butene in the raw material gas or the amount of by-products tends to increase.

As examples of the raw material gas, may be used a fraction containing n-butene as a main component (raffinate 2) obtained by separating butadiene and i-butene from a C4 fraction (a fraction of compounds having 4 carbon atoms) by-produced by naphtha cracking, or a butene fraction generated by a dehydrogenation reaction or an oxidative dehydrogenation reaction of n-butane. Also, gases containing high purity 1-butene, cis-2-butene and trans-2-butene obtained by dimerization of ethylene and mixtures thereof may be used. A gas (hereinafter, sometimes abbreviated as "FCC-C4") containing a large amount of hydrocarbons having 4 carbon atoms obtained from fluid catalytic cracking (Fluid Catalytic Cracking) by decomposing a heavy oil fraction, obtained when crude oil is distilled in a petroleum refining plant or the like, in a fluidized bed state using a powdery solid catalyst to be converted into a hydrocarbon having a low boiling point can be used as a raw material gas as it is, or a material obtained by removing impurities such as phosphorus from FCC-C4 can also be used as a raw material gas.

Molecular Oxygen-Containing Gas:

The molecular oxygen-containing gas is usually a gas containing at least 10% by volume of molecular oxygen ($O_2$). In this molecular oxygen-containing gas, the concentration of molecular oxygen may preferably be not less than 15% by volume, more preferably not less than 20% by volume.

The molecular oxygen-containing gas may contain an optional gas such as molecular nitrogen ($N_2$), argon (Ar), neon (Ne), helium (He), carbon monoxide (CO), carbon dioxide ($CO_2$) and water (water vapor), together with molecular oxygen. The amount of the optional gas in the molecular oxygen-containing gas is usually not more than 90% by volume, preferably not more than 85% by volume, more preferably not more than 80% by volume, when the optional gas is molecular nitrogen, and is usually not more than 10% by volume, preferably not more than 1% by volume, when the optional gas is a gas other than molecular nitrogen. If the amount of the optional gas contained is too large, molecular oxygen of a required amount may be prevented from coexisting with the raw material gas in the reaction system (inside of the reactor vessel 1).

In the first step, as preferred specific examples of the molecular oxygen-containing gas, air may be mentioned.

Inert Gasses:

The inert gases may preferably be supplied to the reactor vessel 1 together with the raw material gas and the molecular oxygen-containing gas.

The supply of inert gases to the reactor vessel 1 can lead to adjust the concentrations (relative concentrations) of the raw material gas and the molecular oxygen so that the mixed gas does not form a detonating gas in the reactor vessel 1.

As examples of the inert gases used in the process of producing butadiene, may be mentioned molecular nitrogen ($N_2$), argon (Ar) and carbon dioxide ($CO_2$). These gasses may be used either singly or in any combination thereof. Among these, molecular nitrogen is preferable from an economic viewpoint.

Water (Water Vapor):

Water may preferably be supplied to the reactor vessel 1 together with the raw material gas and the molecular oxygen-containing gas.

Similarly to the foregoing inert gasses, the supply of water to the reactor vessel 1 can lead to adjust the concentrations (relative concentrations) of the raw material gas and the molecular oxygen so that the mixed gas does not form a detonating gas in the reactor vessel 1.

Mixed Gas:

Since the mixed gas contains a combustible raw material gas and molecular oxygen, its composition is adjusted so that the concentration of the raw material gas does not fall within an explosion range.

Specifically, the composition of the mixed gas at the gas inlet of the reactor vessel 1 is controlled while monitoring the flow rates of respective gases (specifically, the raw material gas, the molecular oxygen-containing gas (air), and inert gases and water (water vapor) used as necessary) constituting the mixed gas by flow meters (not shown), which are installed in the pipings through which the gases are supplied to the reactor vessel 1 (including a piping (not illustrated) communicating with the piping 100 and the piping 112). For example, depending on the molecular oxygen concentration of the recirculation gas supplied to the reactor vessel 1 via the piping 112, the composition of the new supply gas to be supplied to the reactor vessel 1 via the piping 100 is controlled.

In this specification, the "explosion range" indicates a range in which the mixed gas has a composition such that it ignites in the presence of some ignition source. Herein, it is known that the combustible gas does not ignite even with an ignition source when the concentration of the combustible gas is lower than a certain value, and this concentration is referred to as a lower explosion limit. The lower explosion limit is the lower limit of the explosion range. It is also known that, when the concentration of the combustible gas is higher than a certain value, the combustible gas does not ignite even with an ignition source, and this concentration is referred to as an upper explosion limit. The upper explosion limit is the upper limit of the explosion range. Then, these values depend on the concentration of molecular oxygen, and generally, as the concentration of molecular oxygen is lower, both values become closer to each other. When the concentration of molecular oxygen reaches a certain value, both values coincide with each other. The concentration of molecular oxygen at this time is referred to as the maximum safe percentage of oxygen. Thus, if the concentration of molecular oxygen is lower than the maximum safe percentage of oxygen, the mixed gas does not ignite regardless of the concentration of the raw material gas.

Specifically, the concentration of the sum of 1-butene and 2-butene in the mixed gas may preferably be not less than 2% by volume and not more than 30% by volume, more preferably not less than 3% by volume and not more than 25% by volume, and particularly preferably not less than 5% by volume and not more than 20% by volume, per 100% by volume of the mixed gas, from the viewpoint of the productivity of butadiene and the suppression of burden on the metal oxide catalyst. If the concentration of the sum of 1-butene and 2-butene is too small, the productivity of butadiene may decrease. On the other hand, if the concentration of the sum of 1-butene and 2-butene is too large, burden on the metal oxide catalyst may increase.

The concentration (relative concentration) of molecular oxygen relative to the raw material gas in the mixed gas may preferably be not less than 50 parts by volume and not more than 170 parts by volume, more preferably not less than 70 parts by volume and not more than 160 parts by volume, per 100 parts by volume of the raw material gas. If the concentration of molecular oxygen in the mixed gas deviates from the above-described range, it tends to be difficult to adjust the concentration of molecular oxygen at the gas outlet of the reactor vessel 1 by adjusting the reaction temperature. Then, if the concentration of molecular oxygen at the gas outlet of the reactor vessel 1 cannot be controlled by the reaction temperature, the decomposition of the target product and the occurrence of side reactions inside the reactor vessel 1 may not be suppressed.

The concentration (relative concentration) of molecular nitrogen to the raw material gas in the mixed gas may preferably be not less than 400 parts by volume and not more than 1800 parts by volume, more preferably not less than 500 parts by volume and not more than 1700 parts by volume, per 100 parts by volume of the raw material gas. The concentration (relative concentration) of water (water vapor) relative to the raw material gas may preferably be 0 parts by volume or more and not more than 900 parts by volume, more preferably not less than 80 parts by volume and not more than 300 parts by volume, per 100 parts by volume of the raw material gas. If the concentration of molecular nitrogen and the concentration of water are too large, as the value becomes larger, the concentration of the raw material gas becomes smaller in any case. Thus, the production efficiency of butadiene tends to decrease. On the other hand, if the concentration of molecular nitrogen and the concentration of water are too small, as the values become smaller, the concentration of the raw material gas tends to fall within an explosion range in any case, or heat removal in the reaction system, which will be described later, tends to be difficult.

Metal Oxide Catalyst:

The metal oxide catalyst is not particularly limited as long as it functions as an oxidative dehydrogenation catalyst for the raw material gas, and known catalysts can be used. As examples thereof, may be mentioned those containing a metal oxide having at least molybdenum (Mo), bismuth (Bi) and iron (Fe). As preferred specific examples of this metal oxide, may be mentioned a composite metal oxide represented by the following composition formula (1).

Composition formula (1):

In the above-described composition formula (1), X is at least one selected from the group consisting of Ni and Co. Y is at least one selected from the group consisting of Li, Na, K, Rb, Cs and Tl. Z is at least one selected from the group consisting of Mg, Ca, Ce, Zn, Cr, Sb, As, B, P and W. a, b, c, d, e, f and g each independently indicate an atomic ratio of each element. When a is 12, b is 0.1 to 8, c is 0.1 to 20, d is 0 to 20, e is 0 to 4, f is 0 to 2, and g is the number of atoms of the oxygen element required to satisfy the atomic valence of each of the above-described components.

The metal oxide catalyst containing the composite metal oxide represented by the above-described composition formula (1) is highly active and highly selective in the process of producing butadiene using an oxidative dehydrogenation reaction, and is further excellent in stability of life.

The process of preparing the metal oxide catalyst is not particularly limited, and a known method such as an evaporation drying method, a spray drying method, or an oxide mixing method using a raw material of each element relating to a metal oxide constituting a metal oxide catalyst to be prepared may be adopted.

The raw material of each of the above-described elements is not particularly limited, and examples thereof include an oxide, a nitrate, a carbonate, an ammonium salt, a hydroxide, a carboxylic acid salt, an ammonium carboxylate salt, an ammonium halide salt, a hydroacid, and an alkoxide of the component element.

The metal oxide catalyst used may be supported on an inert carrier. Examples of the carrier include silica, alumina, and silicon carbide.

Oxidative Dehydrogenation Reaction:

In the first step, when the oxidative dehydrogenation reaction is started, it is preferable that, first, the supply of the molecular oxygen-containing gas, inert gases and water (water vapor) to the reactor vessel 1 is started and the supply amounts thereof are adjusted so that the concentration of the molecular oxygen at the gas inlet of the reactor vessel 1 is not more than the maximum safe percentage of oxygen, and then the supply of the raw material gas is started, and the supply amount of the raw material gas and the supply amount of the molecular oxygen-containing gas are increased so that the concentration of the raw material gas at the gas inlet of the reactor vessel 1 exceeds the upper explosion limit.

When the supply amounts of the raw material gas and the molecular oxygen-containing gas are increased, the supply amount of the mixed gas may be made constant by reducing the supply amount of water (water vapor). This adjustment can keep the gas residence time in the pipings and the reactor vessel 1 constant, and suppress the fluctuation of the pressure of the reactor vessel 1.

The pressure of the reactor vessel 1 (specifically, the pressure at the gas inlet of the reactor vessel 1), that is, the pressure in the first step, may preferably be not less than 0.1 MPaG and not more than 0.4 MPaG, more preferably not less than 0.15 MPaG and not more than 0.35 MPaG, more preferably not less than 0.2 MPaG and not more than 0.3 MPaG.

When the pressure in the first step is set to fall within the above-described range, the reaction efficiency in the oxidative dehydrogenation reaction is improved.

On the other hand, if the pressure in the first step is too small, the reaction efficiency in the oxidative dehydrogenation reaction tends to decrease. If the pressure in the first step is too large, the yield in the oxidative dehydrogenation reaction tends to decrease.

The gas hourly space velocity (GHSV) determined by the following equation (1) in the oxidative dehydrogenation reaction may preferably be not less than 500 h$^{-1}$ and not more than 5000 h$^{-1}$, more preferably not less than 800 h$^{-1}$ and not more than 3000 h$^{-1}$, more preferably not less than 1000 h$^{-1}$ and not more than 2500 h$^{-1}$.

When the GHSV is set to fall within the above-described range, the reaction efficiency in the oxidative dehydrogenation reaction can be further improved.

GHSV[h$^{-1}$]=gas flow rate in terms of an atmospheric pressure converted value[Nm$^3$/h]/volume of catalyst layer [m$^3$]   Equation (1):

In the above-described equation (1), "volume of catalyst layer" indicates a volume (apparent volume) of the entire catalyst layer containing voids.

The real volume gas hourly space velocity (real volume GHSV) determined by the following equation (2) in the oxidative dehydrogenation reaction may preferably be not less than 500 h$^{-1}$ and not more than 2300 h$^{-1}$, more preferably not less than 600 h$^{-1}$ and not more than 2000 h$^{-1}$, more preferably not less than 700 h$^{-1}$ and not more than 1500 h$^{-1}$.

When the actual volume GHSV is set to fall within the above-described range, the reaction efficiency in the oxidative dehydrogenation reaction can be further improved.

Actual volume GHSV[h$^{-1}$]=actual flow rate[m$^3$/h]/volume of catalyst layer[m$^3$]   Equation (2):

In the above-described equation (2), "volume of catalyst layer" indicates a volume (apparent volume) of the entire catalyst layer containing voids, as in the above-described equation (1).

In the oxidative dehydrogenation reaction, since the oxidative dehydrogenation reaction is an exothermic reaction, the temperature in the reaction system increases, and a plurality of types of by-products may be generated. Then, as by-products, unsaturated carbonyl compounds having 3 to 4 carbon atoms, such as acrolein, acrylic acid, methacrolein, methacrylic acid, maleic acid, fumaric acid, maleic anhydride, methyl vinyl ketone, crotonaldehyde and crotonic acid may be generated, and various adverse effects may occur due to increased concentration thereof in the produced gases. Specifically, since the above-mentioned unsaturated carbonyl compounds are dissolved in the absorbing solvent or the like to be circulated and used in the third step, impurities accumulate in the absorbing solvent or the like, and so precipitation of adhering substances in each member tends to be induced.

Thus, as a method of setting the concentration of the above-mentioned unsaturated carbonyl compounds to fall within a certain range in the oxidative dehydrogenation reaction, may be mentioned a method of adjusting the reaction temperature during the oxidative dehydrogenation reaction. The adjustment of the reaction temperature can confine the concentration of molecular oxygen at the gas outlet of the reactor vessel 1 within a certain range.

Specifically, the reaction temperature may preferably be not lower than 300° C. and not higher than 400° C., more preferably not lower than 320° C. and not higher than 380° C.

When the reaction temperature is set to fall within the above-described range, coking (precipitation of solid carbon) in the metal oxide catalyst can be suppressed, and at the same time, the concentration of the above-mentioned unsaturated carbonyl compounds in the produced gases can be set to fall within a certain range. The concentration of molecular oxygen at the gas outlet of the reactor vessel 1 can also be set to fall within a certain range.

On the other hand, if the reaction temperature is too low, the conversion rate of 1-butene and 2-butene may decrease. There is a tendency that the concentration of the above-mentioned unsaturated carbonyl compounds may increase, impurities may accumulate in the absorbing solvent or the like, or coking in a metal oxide catalyst may occur.

Herein, as a preferable specific example of a method of adjusting the reaction temperature, may be mentioned a method of appropriately cooling the reactor vessel 1 by performing heat removal by, for example, a heat medium (specifically, dibenzyltoluene, nitrite, or the like) to control the temperature of the catalyst layer to be constant.

Produced Gasses:

The produced gases include by-products, an unreacted raw material gas, unreacted molecular oxygen, inert gases and water (water vapor) together with 1,3-butadiene which is a target product obtained from the oxidative dehydrogenation reaction of the raw material gas and the molecular oxygen-containing gas.

In addition to the unsaturated carbonyl compounds having 3 to 4 carbon atoms described above, examples of the by-products may include acetaldehyde, benzaldehyde, acetophenone, benzophenone, fluorenone, anthraquinone, phthalic acid, tetrahydrophthalic acid, isophthalic acid, terephthalic acid, methacrylic acid, phenol and benzoic acid.

The concentration of the molecular nitrogen in the produced gases flowing out of the reactor vessel 1 may preferably be not less than 35% by volume and not more than 90% by volume, more preferably not less than 45% by volume and not more than 80% by volume. The concentration of water (water vapor) may preferably be not less than 5% by volume and not more than 60% by volume, more preferably not less than 8% by volume and not more than 40% by volume. The concentration of butadiene may preferably be not less than 2% by volume and not more than 15% by volume, more preferably not less than 3% by volume and not more than 10% by volume. The concentration of the sum of 1-butene and 2-butene may preferably 0% by volume or more and not more than 2% by volume, more preferably not more than 0.1% by volume and not more than 1.8% by volume.

When the concentration of each component in the produced gases falls within the above-described range, the efficiency of butadiene purification performed in the next and subsequent steps can be improved, and the side reactions of butadiene occurring during purification can be suppressed, whereby the energy consumption in producing butadiene can be further reduced.

Second Step:

In the second step, the produced gases obtained in the first step are cooled. In this second step, cooling of the produced gases from the first step is usually performed by a quenching tower 2 and a heat exchanger 3, as illustrated in the FIGURE.

Specifically, the produced gases from the first step, that is, the produced gases flowing out of the reactor vessel 1 are fed to the quenching tower 2 via the piping 101. After being cooled in the quenching tower 2, the produced gases are fed to the heat exchanger 3 via the piping 104 to be further cooled in the heat exchanger 3. The produced gases from the first step and having been cooled by the quenching tower 2 and the heat exchanger 3 flow out of the heat exchanger 3 into the piping 105.

Thus, the produced gasses from the first step are subjected to this second step for purification. Specifically, a portion of the by-products contained in the produced gases from the first step is removed.

Quenching Tower:

The quenching tower 2 is configured to bring the produced gases from the first step into contact with a cooling medium in a countercurrent flow manner to cool the produced gases to a temperature of about not lower than 30° C. and not higher than 90° C. A gas inlet for introducing the produced gases from the first step is provided in the lower portion of the quenching tower 2. A medium inlet for introducing a cooling medium is provided in the upper portion of the quenching tower 2. The piping 101 having one end connected to the gas outlet of the reactor vessel 1 is connected to the gas inlet. A piping 102 is connected to the medium inlet. A gas outlet for discharging the produced gases having been cooled by the cooling medium is provided at the tower top of the quenching tower 2. A medium outlet for discharging the cooling medium having been in contact (countercurrent contact) with the produced gases from the first step is provided at the tower bottom of the quenching tower 2. A piping 104 is connected to the gas outlet, and a piping 103 is connected to the medium outlet.

In the quenching tower 2, for example, water or an aqueous alkali solution is used as the cooling medium.

The temperature of the cooling medium (temperature at the medium inlet) is appropriately determined depending on the cooling temperature, and may preferably be not lower than 10° C. and not higher than 90° C., more preferably not lower than 20° C. and not higher than 70° C., and particularly preferably not lower than 20° C. and not higher than 40° C.

In the quenching tower 2 during operation, the temperature inside the quenching tower 2 may preferably be not lower than 10° C. and not higher than 100° C., more preferably not lower than 20° C. and not higher than 90° C.

The pressure of the quenching tower 2 during operation (specifically, the pressure of the gas outlet of the quenching tower 2), that is, the pressure in the second step may preferably be equivalent to the pressure in the first step or less than the pressure in the first step.

Specifically, a difference between the pressure in the second step and the pressure in the first step, that is, a value obtained by subtracting the pressure in the second step from the pressure in the first step may preferably be 0 MPaG or more and not more than 0.05 MPaG, more preferably not less than 0.01 MPaG and not more than 0.04 MPaG.

When the pressure difference between the first step and the second step is set to fall within the above-described range, condensation of the by-products in the produced gases from the first step and dissolution thereof into the cooling medium can be promoted in the quenching tower 2. As a result, the by-products in the produced gases flowing out of the quenching tower 2 (specifically, the concentration of ketones and aldehydes, which will be described later) can be reduced in amount.

The produced gases flowing out of the quenching tower 2 include, in addition to butadiene, 1-butene, 2-butene, molecular oxygen, inert gases and water (water vapor), and may also include ketones, aldehydes and the like.

Herein, the ketones and aldehydes contained in the produced gases flowing out of the quenching tower 2 are at least one compound selected from the group consisting of methyl vinyl ketone, acetaldehyde, acrolein, methacrolein, crotonaldehyde, benzaldehyde, acetophenone and benzophenone.

The concentration of molecular nitrogen in the produced gases flowing out of this quenching tower 2 may preferably be not less than 60% by volume and not more than 94% by volume, more preferably not less than 70% by volume and not more than 90% by volume. The concentration of the sum of 1-butene and 2-butene may preferably be 0% by volume or more and not more than 2% by volume, more preferably not less than 0.1% by volume and not more than 1.8% by volume. The concentration of butadiene may preferably be not less than 2% by volume and not more than 15% by volume, more preferably not less than 3% by volume and not more than 10% by volume. The concentration of water (water vapor) may preferably be not less than 5% by volume and not more than 60% by volume, more preferably not less than 10% by volume and not more than 45% by volume. The concentration of the ketones and aldehydes may preferably be 0% by volume or more and not more than 0.3% by volume, more preferably not less than 0.05% by volume and not more than 0.25% by volume.

The cooling medium flowing out of the quenching tower 2 having been in contact with the produced gases from the first step includes the by-products in the produced gases from the first step, which have been condensed in the quenching tower 2 or dissolved in the cooling medium, and specifically is considered to contain organic acids.

The organic acids contained in the cooling medium flowing out of the quenching tower 2 are at least one compound selected from the group consisting of maleic acid, fumaric acid, acrylic acid, phthalic acid, benzoic acid, crotonic acid, tetrahydrophthalic acid, isophthalic acid, terephthalic acid, methacrylic acid and phenol.

The concentration of the organic acids in the cooling medium flowing out of this quenching tower 2 may preferably be 0% by mass or more and not more than 7% by mass, more preferably not less than 1% by volume and not more than 6% by volume.

If the concentration of the organic acids is too large, the load on the waste water treatment may increase.

Heat Exchanger:

As the heat exchanger 3, an appropriate heat exchanger capable of cooling the produced gases flowing out of the quenching tower 2 to room temperature (not lower than 10° C. and not higher than 30° C.) is used.

In the illustrated example, the heat exchanger 3 has a gas inlet to which the piping 104 having one end connected to the gas outlet of the quenching tower 2 is connected, and a gas outlet to which a piping 105 is connected.

The pressure in the heat exchanger 3 during operation (specifically, the pressure at the gas outlet of the heat exchanger 3) may preferably be equivalent to the pressure of the quenching tower 2 during operation (the pressure at the gas outlet of the quenching tower 2).

The concentration of the molecular nitrogen in the produced gases flowing out of the heat exchanger 3 may preferably be not less than 60% by volume and not more than 94% by volume, more preferably not less than 70% by volume and not more than 85% by volume. The concentration of the sum of 1-butene and 2-butene may preferably be 0% by volume or more and not more than 2% by volume, more preferably not less than 0.1% by volume and not more than 1.8% by volume. The concentration of butadiene may preferably be not less than 2% by volume and not more than 15% by volume, more preferably not less than 3% by volume and not more than 10% by volume. The concentration of the ketones and aldehydes may preferably be 0% by volume or more and not more than 0.3% by volume, more preferably not less than 0.05% by volume and not more than 0.25% by volume. Then, the concentration of methyl vinyl ketone constituting the ketones and aldehydes is 0% by volume or more and not more than 0.03% by volume as described above.

When the concentration of each component in the produced gases having been cooled in the second step falls within the above-described range, the efficiency of butadiene purification in the next and subsequent steps can be improved and the side reactions occurring in the desolventizing step can be suppressed, whereby the energy consumption in producing butadiene can be further reduced.

Third Step:

In the third step, the produced gases having undergone the second step are separated (crude separation) into molecular oxygen and inert gases and other gases containing 1,3-butadiene by selective absorption into an absorbing solvent. As used herein the term "other gases containing 1,3-butadiene" refers to gases containing at least butadiene and 1-butene and 2-butene (unreacted 1-butene and 2-butene), which are absorbed by an absorbing solvent.

In this third step, the separation of the produced gases having undergone the second step is performed by an absorption tower 4, as illustrated in the FIGURE. Here, the absorption tower 4 has a gas inlet for introducing the produced gases having undergone the second step at a lower portion, and a solvent inlet for introducing the absorbing solvent at an upper portion. The absorption tower 4 also has a solvent outlet for discharging the absorbing solvent that has absorbed gases (specifically, other gases containing 1,3-butadiene) at the tower bottom, and a gas outlet for discharging gases (specifically, molecular oxygen and inert gases) that have not been absorbed by the absorbing solvent at the tower top. A piping 105 having one end connected to the gas outlet of the heat exchanger 3 is connected to the gas inlet, and a piping 106 is connected to the solvent inlet. A piping 113 is connected to the solvent outlet, and a piping 107 is connected to the gas outlet.

The third step will now be specifically described. The produced gases having undergone the second step, that is, the produced gases flowing out of the heat exchanger 3 are fed to the absorption tower 4 via the piping 105, and in synchronization therewith, the absorbing solvent is supplied to the absorption tower 4 via the piping 106. In this manner, the absorbing solvent is brought into countercurrent contact with the produced gases having undergone the second step, and so the other gases containing 1,3-butadiene in the produced gases having undergone the second step are selectively absorbed by the absorbing solvent, whereby the other gases containing 1,3-butadiene, and the molecular oxygen and inert gases are roughly separated. Then, the absorbing solvent that has absorbed the other gases containing 1,3-butadiene flows out of the absorption tower 4 into the piping 113, while the molecular oxygen and inert gases that have not been absorbed by the absorbing solvent flow out of the absorption tower 4 into the piping 107.

In the absorption tower 4 during operation, the temperature inside the absorption tower 4 is not particularly limited, but molecular oxygen and inert gases are hardly absorbed by the absorbing solvent as the temperature inside the absorption tower 4 increases. On the other hand, the absorption efficiency of hydrocarbons such as butadiene (other gases containing 1,3-butadiene) into the absorbing solvent increases as the temperature inside the absorption tower 4 decreases. Therefore, the temperature may preferably be not lower than 0° C. and not higher than 60° C., more preferably not lower than 10° C. and not higher than 50° C., in consideration of the productivity of butadiene.

The pressure of the absorption tower 4 during operation (specifically, the pressure at the gas outlet of the absorption tower 4), that is, the pressure in the third step may preferably be equivalent to the pressure in the second step or less than the pressure in the second step.

Specifically, a difference between the pressure in the third step and the pressure in the second step, that is, a value obtained by subtracting the pressure in the third step from the pressure in the second step may preferably be 0 MPaG or more and not more than 0.05 MPaG, more preferably not less than 0.01 MPaG and not more than 0.04 MPaG.

When the pressure difference between the second step and the third step is set to fall within the above-described range, absorption of butadiene (other gases containing 1,3-butadiene) into the absorbing solvent in the absorption tower 4 can be promoted. As a result, the amount of the absorbing solvent used can be reduced and energy consumption can be reduced.

Absorbing Solvent:

Examples of the absorbing solvent include those containing an organic solvent as a main component. Herein, "containing an organic solvent as a main component" indicates that the content ratio of the organic solvent in the absorbing solvent is not less than 50% by mass.

As examples of the organic solvent constituting the absorbing solvent, may be mentioned an aromatic compound such as toluene, xylene and benzene, an amide compound such as dimethylformamide and N-methyl-2-pyrrolidone, a sulfur compound such as dimethyl sulfoxide and sulfolane, a nitrile compound such as acetonitrile and butyronitrile and a ketone compound such as cyclohexanone and acetophenone.

The amount of the absorbing solvent to be used (supply amount) is not particularly limited, but may preferably be not less than 10 times by mass and not more than 100 times by mass, more preferably not more than 17 times by mass and not more than 35 times by mass, relative to the flow rate (mass flow rate) of the sum of butadiene and 1-butene and 2-butene in the produced gases having undergone the second step.

When the amount of the absorbing solvent to be used is set to fall within the above-described range, the absorption efficiency of other gases containing 1,3-butadiene can be improved.

On the other hand, if the amount of the absorbing solvent to be used is too large, the energy consumption used in purification for circulating and using the absorbing solvent tends to increase. If the amount of the absorbing solvent to be used is too small, the absorption efficiency of other gases containing 1,3-butadiene tends to decrease.

The temperature (temperature at the solvent inlet) of the absorbing solvent may preferably be not lower than 0° C. and not higher than 60° C., more preferably not lower than 0° C. and not higher than 60° C.

When the temperature of the absorbing solvent is set to fall within the above-described range, the absorption efficiency of other gases containing 1,3-butadiene can be further improved.

Circulation Step:

In the circulation step, the molecular oxygen and inert gases obtained in the third step are fed as a recirculation gas to the first step. In this circulation step, the molecular oxygen and inert gases from the third step are processed by a solvent recovery tower 5 and a compressor 6.

More specifically, the molecular oxygen and inert gases from the third step, that is, the molecular oxygen and inert gases flowing out of the absorption tower 4 are fed to the solvent recovery tower 5 via the piping 107 and subjected to a solvent removal treatment. Then, they are fed to the compressor 6 via a piping 110, and subjected to a pressure adjustment treatment as necessary. The molecular oxygen and inert gases from the third step thus having been subjected to the solvent removal treatment and the pressure adjustment treatment flow out of the compressor 6 into the piping 112 toward the reactor tower 1.

In the illustrated example, regarding the molecular oxygen and inert gases flowing out of the solvent recovery tower 5, a portion of the molecular oxygen and inert gases is disposed of in the course of flowing via the piping 110 through a piping 111 which is communicated with the piping 110. As described above, the piping 111 for disposing of a portion of the molecular oxygen and inert gases flowing out of the solvent recovery tower 5 is provided, and so the supply amount of the recirculation gas supplied to the first step can be adjusted.

Solvent Recovery Tower:

The solvent recovery tower 5 is configured such that the molecular oxygen and inert gases from the third step are cleaned by water or a solvent, thereby subjecting the molecular oxygen and inert gases to a solvent removal treatment. A gas inlet for introducing the molecular oxygen and inert gases from the third step is provided at a central portion of the solvent recovery tower 5. A cleaning liquid inlet for introducing water or a solvent is provided at an upper portion of the solvent recovery tower 5. The piping 107 having one end connected to the gas outlet of the absorption tower 4 is connected to the gas inlet, and a piping 108 is connected to the cleaning liquid inlet. In the solvent recovery tower 5, a gas outlet for discharging the molecular oxygen and inert gases having been cleaned by water or a solvent is provided at the tower top thereof. A cleaning liquid outlet for discharging water or a solvent used for cleaning the molecular oxygen and inert gases from the third step is provided at the tower bottom of the solvent recovery tower 5. The piping 110 is connected to the gas outlet, and the cleaning liquid outlet is connected to a piping 109.

In this solvent recovery tower 5, the absorbing solvent contained in the molecular oxygen and inert gases from the third step is removed, and the removed absorbing solvent flows out of the cleaning liquid outlet into the piping 109 together with the water or the solvent used for cleaning, and is recovered via the piping 109. The molecular oxygen and inert gases from the third step having been subjected to the solvent removal treatment flow out of the gas outlet of the solvent recovery tower 5 into the piping 110.

In the solvent recovery tower 5 during operation, the temperature inside the solvent recovery tower 5 is not particularly limited, but may preferably be not lower than 0° C. and not higher than 80° C., more preferably not lower than 10° C. and not higher than 60° C.

Compressor:

As the compressor 6, those capable of increasing the pressure of the molecular oxygen and inert gases from the solvent recovery tower 5 as necessary to achieve the required pressure in the first step are appropriately used.

In the illustrated example, the gas inlet of the compressor 6 is connected to the piping 110 having one end connected to the gas outlet of the solvent recovery tower 5, and the gas outlet thereof is connected to the piping 112.

In the compressor 6, when the pressure in the third step is less than the pressure in the first step, the pressure is increased in accordance with the pressure difference between the third step and the first step by the amount of the pressure difference.

In the case where the pressure increase is performed in the compressor 6, the pressure increase is usually small, and so the electrical energy consumption of the compressor remains small.

In the molecular oxygen and inert gases flowing out of the compressor 6, that is, the recirculation gas, the concentration of the molecular nitrogen may preferably be not less than 87% by volume and not more than 97% by volume, more preferably not less than 90% by volume and not more than 95% by volume. The concentration of the molecular oxygen may preferably be not less than 1% by volume and not more than 6% by volume, more preferably not less than 2% by volume and not more than 5% by volume.

Desolventizing Step:

In the desolventizing step, the absorbing solvent obtained in the third step and having absorbed other gases containing 1,3-butadiene is subjected to a solvent separation treatment. That is, separation of the absorbing solvent from the absorbing solvent from the third step can lead to provide a gas stream of other gases containing 1,3-butadiene, that is, a gas containing 1,3-butadiene. In this desolventizing step, as illustrated in the FIGURE, separation of other gases containing 1,3-butadiene and the absorbing solvent is performed by a desolventizing tower 7.

Specifically, the absorbing solvent from the third step, that is, the absorbing solvent having absorbed other gases containing 1,3-butadiene flowing out of the absorption tower 4, is fed to the desolventizing tower 7 via the piping 113 and subjected to the solvent separation treatment. Then, in the desolventizing tower 7, the other gases containing 1,3-butadiene and the absorbing solvent are distilled and separated.

Desolventizing Tower:

The desolventizing tower 7 is configured to distill and separate the absorbing solvent from the third step to perform the solvent separation treatment. A solvent inlet for introducing the absorbing solvent from the third step is provided at a central portion of the desolventizing tower 7. A gas outlet for discharging the gases containing 1,3-butadiene separated from the absorbing solvent from the third step is provided at the tower top in the desolventizing tower 7. At the tower bottom in the desolventizing tower 7, a solvent outlet for discharging the absorbing solvent separated from the absorbing solvent from the third step is provided. A piping 113 having one end connected to the solvent outlet of the absorption tower 4 is connected to the solvent inlet, a piping 115 is connected to the gas outlet, and a piping 114 is connected to the solvent outlet.

In this desolventizing tower 7, the gases containing 1,3-butadiene and the absorbing solvent separated from the absorbing solvent from the third step flow out of the gas outlet into the piping 115, and from the solvent outlet into the piping 114, respectively.

The pressure inside the desolventizing tower 7 is not particularly limited, but the pressure may preferably be not less than 0.03 MPaG and not more than 1.0 MPaG, more preferably not less than 0.2 MPaG and not more than 0.6 MPaG.

In the desolventizing tower 7 during operation, the temperature at the tower bottom of the desolventizing tower 7 may preferably be not lower than 80° C. and not higher than 1900° C., more preferably not lower than 100° C. and not higher than 180° C.

According to the process of producing 1,3-butadiene of the present invention as described above, the use of one having a specific composition as a raw material gas can lead to suppress the production of methyl vinyl ketone which is a by-product of an oxidative dehydrogenation reaction. Therefore, in the desolventizing tower 7 (specifically, a reboiler) used in the desolventizing step, for example, a small amount or a trace amount of an adhering substance (3-cyclohexen-1-carboxaldehyde) derived from acrolein or the like is generated, but generation of an adhering substance derived from methyl vinyl ketone is prevented or suppressed. As a result, the generation of adhering substances in the desolventizing tower 7 (reboiler) used in the desolventizing step can be reduced.

In the process of producing 1,3-butadiene according to the present invention, the pressure in the first step is set to fall within a specific range and the pressures in the second step and the third step are also set to be equal to or lower than the pressure of the preceding step, and so the reaction efficiency of the oxidative dehydrogenation reaction can be improved. The energy consumption required for purifying the produced gases, obtained in the first step, in the second step and subsequent steps can also be reduced.

EXAMPLES

Hereinafter, specific examples of the present invention will be described, but the present invention is not limited to these examples.

An analysis method of gas composition, an analysis method of methyl vinyl ketone, an analysis method of ketones and aldehydes, and an analysis method of organic acids are as follows.

Gas composition analysis was performed by gas chromatography under the conditions shown in Table 1 below. The amount of water (water vapor ($H_2O$)) was calculated by adding the amount of water obtained by a water-cooled trap at the time of gas sampling.

TABLE 1

| Summary of gas composition analysis | | |
|---|---|---|
| Gas species | 1,3-butadiene, n-butene | $N_2$, $O_2$, $CO_x$, $H_2O$ |
| Model | GC-14B | GC-14B |
| | (Manufactured by Shimadzu Corporation) | (Manufactured by Shimadzu Corporation) |
| Detector | FID | TCD |
| Column | TC-BOND Alumina/$Na_2SO_4$ | WG-100 |
| | 0.53 mm I.D. × 30 m df = 10 μm | 6.35 mm I.D. × 1.8 m |
| | (Manufactured by GL Sciences Inc.) | (Manufactured by GL Sciences Inc.) |
| Carrier gas | $N_2$ 40 ml/min | He 50 ml/min |
| Temperature | | |
| injection | 200° C. | 60° C. |
| Detector | 250° C. | 80° C. |
| Column | 60° C. 5 min→135° C. (5° C./min) →185° C. (15° C./min) | 50° C. |

The analysis of methyl vinyl ketone, the analysis of ketones and aldehydes and the analysis of organic acids were performed by liquid chromatography under the conditions shown in Table 2 below.

TABLE 2

| Model | LC-2000Plus |
|---|---|
| | (Manufactured by JASCO Corporation) |
| Detector | UV (210 nm, 230 nm) |
| Column | TSKgel ODS-100V 5 μm |
| | 4.6 mm ID × 15 cm |
| | (Manufactured by TOSOH Corporation) |
| Eluent | Acetonitrile/phosphoric acid water |
| | 0.8 ml/min |
| Column oven | 40° C. |

Example 1

1,3-Butadiene was produced from a raw material gas containing 1-butene and 2-butene by passing through the fallowing first step, second step, third step, desolventizing step and circulation step according to the flow diagram of the FIGURE.

As a raw material gas, a gas containing 1-butene and 2-butene and having a proportion of 87% by volume of 2-butene to the sum of 1-butene and 2-butene, which is defined as 100% by volume, was used.

First Step:

A reactor vessel 1 (inner diameter: 21.2 mm, outer diameter: 25.4 mm) was filled with a metal-oxide catalyst with a catalyst bed length of 4000 mm. A mixed gas having a volume ratio (1-butene and 2-butene/$O_2$/$N_2$/$H_2O$) of 1/1.5/16.3/1.2 was supplied to the reactor vessel 1 at a GHSV of 2000 $h^{-1}$. The raw material gas and the molecular oxygen-containing gas were subjected to an oxidative dehydrogenation reaction under a condition of a reaction temperature of 320 to 350° C., thereby obtaining produced gases containing 1,3-butadiene. The pressure in this first step, that is, the pressure at the gas inlet of the reactor vessel 1, was 0.1 MPaG. Here, the actual volume GHSV of the mixed gas was 2150 $h^{-1}$.

In this first step, as the metal oxide catalyst, one obtained by supporting an oxide represented by the composition formula of $Mo_{12}Bi_5Fe_{0.5}Ni_2Co_3K_{0.1}Cs_{0.1}Sb_{0.2}$ on the spherical silica with a proportion of 20% of the total volume of the catalyst was used.

The composition of the mixed gas was adjusted by mixing the raw material gas and the recirculation gas (molecular oxygen and inert gases), and if necessary, further mixing air as a molecular oxygen-containing gas, molecular nitrogen as inert gases and water (water vapor).

Second Step:

The produced gases discharged from the reactor vessel 1 was quenched in a quenching tower 2 by bringing it into countercurrent contact with water as a cooling medium to be cooled to 76° C., and then cooled to 30° C. in a heat exchanger 3. The pressure in the second step, that is, the pressure at the gas outlet of the quenching tower 2 was 0.1 MPaG, and the pressure at the gas outlet of the heat exchanger 3 was 0.1 MPaG.

In the produced gases flowing out of the heat exchanger 3, the concentration of methyl vinyl ketone was 0.008% by volume (80 volppm), and the concentration of ketones and aldehydes was 0.08% by volume (800 volppm).

In water flowing out of the quenching tower 2 and having been in contact with the produced gases, which was flowed out of the reactor vessel 1, the concentration of the organic acid was 2.5% by mass.

Third Step:

The produced gases flowing out of the heat exchanger 3 (hereinafter also referred to as "cooled produced gases") were supplied from a gas inlet at a lower portion of an absorption tower 4 (outer diameter: 152.4 mm, height: 7800 mm and material: SUS304) in which regular packings were disposed, and an absorbing solvent containing toluene in an amount of not less than 95% by mass was supplied at a temperature of 10° C. from a solvent inlet at an upper portion of the absorption tower 4. The supply amount of the absorbing solvent was 33 times by mass with respect to the flow rate (mass flow rate) of the sum of butadiene and 1-butene and 2-butene in the cooled produced gases. The pressure in this third step, that is, the pressure at the gas outlet of the absorber 4, was 0.1 MPaG.

Circulation Step:

The gases flowing out of the absorption tower 4 were cleaned with water or a solvent in a solvent recovery tower 5 to remove a small amount of absorbing solvent contained in the gases. The gases from which the absorbing solvent had been removed in this manner flowed out of the solvent recovery tower 5, and a part thereof was disposed of, and most of the remaining part was fed to the compressor 6. In the compressor 6, the pressure of the gases from the solvent recovery tower 5 was increased by the pressure adjustment treatment. Thus, the absorbing solvent was removed, and the pressurized gases flowed out of the compressor 6 and were flown back to the reactor vessel 1.

In the gases flowing out of the compressor 6, the concentration of molecular nitrogen was 94% by volume, and the concentration of molecular oxygen was 3% by volume. The gases flowing out of the compressor 6 contained 3% by volume of impurities (specifically, carbon monoxide and carbon dioxide, and the like).

Desolventizing Step:

The liquid flowing out of the absorption tower 4 was supplied to the desolventizing tower 7, and the gases flowing out of the desolventizing tower body was cooled in a condenser, whereby gases containing 1,3-butadiene was obtained. An effluent in which a portion of the liquid flowing out of the desolventizing tower body was heated in a reboiler, that is, an absorbing solvent (hereinafter, also referred to as "circulating absorbing solvent") was also obtained. In this manner, the gases containing 1,3-butadiene and the circulating absorbing solvent were distilled and separated in the desolventizing tower 7.

In the circulating absorbing solvent flowing out of the desolventizing tower 7 (reboiler), the concentration of methyl vinyl ketone was 0.05% by mass (500 wtppm).

In the reboiler, the presence or absence of an adhering substance (solid adhering substance) after a lapse of 500 hours counted from the start of the production of 1,3-butadiene (specifically, the supply of the raw material gas was started) was visually confirmed, and a trace amount of the adhering substance was confirmed. Then, the components of the adhering substance were confirmed by pyrolysis gas chromatography and found to be 4-acetylcyclohexene, 3-cyclohexene-1-carboxaldehyde and butadiene.

Example 2

Butadiene was produced from a raw material gas containing 1-butene and 2-butene in the same manner as that in Example 1 except that, in Example 1, one having the proportion of 75% by volume of 2-butene to the sum of 1-butene and 2-butene, which is defined as 100% by volume was used as the raw material gas, and the pressure and the supply amount of absorbing solvent in the first step were changed as shown in Table 3.

In Example 2, the pressure in the second step, that is, the pressure at the gas outlet of the quenching tower 2 was 0.2 MPaG, and the pressure at the gas outlet of the heat exchanger 3 was 0.2 MPaG.

The components of the adhering substance (solid adhering substance) generated in the reboiler were confirmed by the same method as that in Example 1, and found to be 4-acetylcyclohexene, 3-cyclohexen-1-carboxaldehyde and butadiene.

The values confirmed in the production process are shown in Table 3.

Control Example 1

Butadiene was produced from a raw material gas containing 1-butene in the same manner as that in Example 1 except that, in Example 1, a compressor was disposed and used between the heat exchanger 3 and the absorption tower 4, one having the proportion of 0% by volume of 2-butene to the sum of 1-butene and 2-butene, which is defined as 100% by volume, was used as the raw material gas, and the pressure and the supply amount of absorbing solvent in the first step were changed as shown in Table 3.

The components of the adhering substance (solid adhering substance) generated in the reboiler were confirmed by the same method as in Example 1, and found to be 4-acetylcyclohexene, 3-cyclohexen-1-carboxaldehyde, butadiene and methyl vinyl ketone.

The values confirmed in the production process are shown in Table 3.

TABLE 3

|  | Example1 | Example2 | Control example1 |
|---|---|---|---|
| Proportion of 2-butene to sum of 1-butene and 2-butene (defined as 100 vol %) [vol %] | 87 | 75 | 0 |
| Mixed gas composition Sum of 1-butene and 2-butene/$O_2$/$N_2$/$H_2O$ |  | 1/1.5/16.3/1.2 |  |
| GHSV [$h^{-1}$] | 2000 | 2000 | 2000 |
| Actual volume GHSV [$h^{-1}$] | 2150 | 1450 | 2850 |
| Pressure in the first step [MPaG] | 0.1 | 0.2 | 0.05 |
| Pressure in the second step [MPaG] | 0.1 | 0.2 | 0.05 |
| Concentration of methyl vinyl ketone [vol %] in the produced gases having underdone the second step | 0.008 | 0.02 | 0.09 |

TABLE 3-continued

|  | Example1 | Example2 | Control example1 |
|---|---|---|---|
| Concentration of ketones and aldehydes [vol %] in the produced gases having underdone the second step | 0.08 | 0.28 | 0.15 |
| Concentration of organic acid [mass %] in the cooling medium from the second step | 2.5 | 5 | 1 |
| Presence of a compressor between the second step and the third step | None | None | Yes |
| Supply amount of absorbing solvent: Magnification [times by mass] to the total flow rate (mass flow rate) of butadiene, 1-butene and 2-butene in the cooled produced gases | 33 | 23 | 26 |
| Pressure in the third step [MPaG] | 0.1 | 0.2 | 0.4 |
| Concentration of molecular oxygen in recirculation gas [vol %] | 3 | 3 | 3 |
| Concentration of molecular nitrogen in recirculation gas [vol %] | 94 | 94 | 94 |
| Concentration of methyl vinyl ketone in circulating absorbing solvent [mass %] | 0.05 | 0.1 | 0.5 |
| Presence of solid adhering substances in the heat exchanger for solvent | Very small amount | Small amount | Large amount |
| Electric energy consumption used for pressure increase [kWh/kg of raw material] | 0.15 | 0.1 | 0.7 |

From the results shown in Table 3, it was confirmed that, according to the process of producing 1,3-butadiene of the present invention according to Examples 1 and 2, generation of methyl vinyl ketone can be suppressed, and as a result, generation of adhering substances in a reboiler used in a desolventizing step can be reduced.

According to the process of producing 1,3-butadiene of the present invention according to Examples 1 and 2, it was confirmed that the reaction efficiency of the oxidative dehydrogenation reaction can be improved without providing a compressor between the second step and the third step, and the energy consumption required for purifying the produced gases can also be reduced by setting the pressure in the first step to a specified range of not less than 0.1 MPaG and not more than 0.4 MPaG, and by setting the pressure in the second step and the pressure in the third step to be equal to or lower than the pressure of the preceding step. As compared with the process of producing 1,3-butadiene according to Control Example 1, it was also confirmed that, since the contact time between the produced gases from the first step and the cooling medium in the quenching tower 2 becomes longer, the concentration of the organic acid in the cooling medium flowing out of the quenching tower 2, that is, the removal rate of the by-product in the quenching tower 2 increases.

REFERENCE SIGNS LIST 1 reactor vessel
2 quenching tower
3 heat exchanger
4 absorption tower
5 solvent recovery tower
6 compressor
7 desolventizing tower
100 to 116 piping

The invention claimed is:

1. A process of producing 1,3-butadiene, the process comprising:
  conducting an oxidative dehydrogenation reaction of a raw material gas with a molecular oxygen-containing gas in the presence of a metal oxide catalyst, thereby obtaining gases comprising 1,3-butadiene, the raw material gas comprising 1-butene and 2-butene and having a proportion of 2-butene to a sum of 1-butene and 2-butene, which is defined as 100% by volume, being not less than 50% by volume;
  cooling the gases; and
  separating cooled gases into molecular oxygen and inert gases and other gases comprising 1,3-butadiene by selective absorption to an absorbing solvent,
  wherein a concentration of methyl vinyl ketone in the cooled gases is 0% by volume or more and not more than 0.03% by volume,
  wherein a first pressure in the conducting is not less than 0.1 MPaG and not more than 0.4 MPaG,
  wherein a second pressure in the cooling is not more than the first pressure, and
  wherein a third pressure in the separating is not more than the second pressure.

2. The process of claim 1, wherein, in the cooled gases:
  a concentration of molecular nitrogen is not less than 60% by volume and not more than 94% by volume,
  a concentration of the sum of 1-butene and 2-butene is 0% by volume or more and not more than 2% by volume,
  a concentration of 1,3-butadiene is not less than 2% by volume and not more than 15% by volume, and
  a concentration of ketones and aldehydes is 0% by volume or more and not more than 0.3% by volume.

3. The process of claim 1, wherein, in the cooling, the gases are cooled by being brought into contact with a cooling medium, and a concentration of an organic acid in the cooling medium having been in contact with the gases is not more than 7% by mass.

4. The process of claim 1, wherein the first pressure in the conducting is not less than 0.15 MPaG and not more than 0.4 MPaG.

5. The process of claim 1, wherein the molecular oxygen and inert gases is flown back to the conducting, and
  wherein a concentration of molecular nitrogen in the gases to be flown back from the separating to the cooling is not less than 87% by volume and not more than 97% by volume, and a concentration of the molecular oxygen therein is not less than 1% by volume and not more than 6% by volume.

6. The process of claim 1, wherein the first pressure in the conducting is not less than 0.2 MPaG and not more than 0.4 MPaG.

7. The process of claim 1, wherein the first pressure in the conducting is not less than 0.1 MPaG and not more than 0.35 MPaG.

8. The process of claim 1, wherein the first pressure in the conducting is not less than 0.1 MPaG and not more than 0.3 MPaG.

9. The process of claim 1, wherein the first pressure in the conducting is not less than 0.2 MPaG and not more than 0.3 MPaG.

10. The process of claim 1, wherein a concentration of the sum of the 1-butene and the 2-butene in the raw material gas is not less than 75% by volume.

11. The process of claim 1, wherein a concentration of the sum of the 1-butene and the 2-butene in the raw material gas is not less than 95% by volume.

12. The process of claim 1, wherein the proportion of 2-butene to a sum of 1-butene and 2-butene in the raw material gas is not less than 75% by volume.

13. The process of claim 1, wherein the proportion of 2-butene to a sum of 1-butene and 2-butene in the raw material gas is not less than 87% by volume.

14. The process of claim 1, wherein a difference in pressure between the separating to the cooling is 0 MPaG or more and not more than 0.05 MPaG.

15. The process of claim 1, wherein a difference in pressure between the separating to the cooling is 0.01 MPaG or more and not more than 0.04 MPaG.

16. The process of claim 1, wherein the raw material gas comprises not more than 25% by volume impurities, per 100% by volume of the raw material gas.

17. The process of claim 1, wherein the raw material gas comprises not more than 5% by volume impurities, per 100% by volume of the raw material gas.

18. The process of claim 1, wherein the concentration of the methyl vinyl ketone in the cooled gases is 0% by volume or more and not more than 0.028% by volume.

19. The process of claim 1, wherein the concentration of the methyl vinyl ketone in the cooled gases is 0% by volume or more and not more than 0.008% by volume.

20. The process of claim 1, wherein the absorbing solvent is not less than 10 times by mass and not more than 100 times by mass, relative to a mass flow rate of the sum of the butadiene, 1-butene, and 2-butene in gases produced after the cooling.

* * * * *

UNITED STATES PATENT AND TRADEMARK OFFICE
CERTIFICATE OF CORRECTION

| | |
|---|---|
| PATENT NO. | : 11,230,513 B2 |
| APPLICATION NO. | : 17/013028 |
| DATED | : January 25, 2022 |
| INVENTOR(S) | : Sugimoto et al. |

It is certified that error appears in the above-identified patent and that said Letters Patent is hereby corrected as shown below:

On the Title Page

Item (30), the Foreign Application Priority Data information has been omitted. Item (30) should read:
--Foreign Application Priority Data
(30) Mar. 06, 2018 (JP)............................2018-039549--

Signed and Sealed this
Seventh Day of June, 2022

Katherine Kelly Vidal
*Director of the United States Patent and Trademark Office*